United States Patent [19]

Miyauchi

[11] Patent Number: 4,900,730

[45] Date of Patent: Feb. 13, 1990

[54] PREPARATION WHICH PROMOTES THE ABSORPTION OF PEPTIDES

[75] Inventor: Yasuyo Miyauchi, Yokohama, Japan

[73] Assignee: Toyo Jozo Co., Ltd., Shizuoka, Japan

[21] Appl. No.: 63,744

[22] Filed: Jun. 18, 1987

Related U.S. Application Data

[63] Continuation of Ser. No. 628,317, Jul. 6, 1984, abandoned, which is a continuation-in-part of Ser. No. 342,079, Jan. 25, 1982, abandoned.

[30] Foreign Application Priority Data

| Jan. 14, 1981 | [JP] | Japan | 56-3263 |
| Mar. 6, 1981 | [JP] | Japan | 56-32951 |
| Nov. 11, 1981 | [JP] | Japan | 56-181508 |
| Jan. 11, 1982 | [SE] | Sweden | 8200103 |
| Jan. 11, 1982 | [GB] | United Kingdom | 8200670 |
| Jan. 12, 1982 | [FR] | France | 8200357 |
| Jan. 13, 1982 | [CA] | Canada | 394029 |
| Jan. 13, 1982 | [DE] | Fed. Rep. of Germany | 3200766 |
| Jan. 13, 1982 | [IT] | Italy | 19097 A/82 |

[51] Int. Cl.$^4$ .................. A61K 37/30; A61K 37/02; A61K 9/02

[52] U.S. Cl. ......................................... 514/12; 514/2; 514/808; 514/8; 514/946; 514/947; 514/966; 424/436; 424/DIG. 15

[58] Field of Search ............... 514/2, 8, 12, 808, 946, 514/966, 947, 553, 557, 558, 560, 561, 562, 564, 566; 424/153, DIG. 15, 436

[56] References Cited

U.S. PATENT DOCUMENTS

| 3,849,388 | 11/1974 | Rittel et al. | 514/808 |
| 4,405,597 | 9/1983 | Takagishi et al. | 424/436 |
| 4,609,640 | 9/1986 | Morishita et al. | 514/12 |

FOREIGN PATENT DOCUMENTS

| 31561 | 8/1981 | European Pat. Off. . |
| 7144214 | 9/1982 | Japan . |
| 2092002 | 8/1982 | United Kingdom . |

OTHER PUBLICATIONS

Doepfner, cited in Chem. Abstracts, vol. 78, 1973 115232e.

The Pharmaceutical Codex, "Injections," pp. 446-449 (1979).

Stekol'nikov et al., cited in Chem. Abstracts, vol. 74:49907j (1971).

*Primary Examiner*—Jacqueline M. Stone
*Attorney, Agent, or Firm*—Antonelli, Terry & Wands

[57] ABSTRACT

Medicinal compositions containing a water soluble absorption promoter having chelating activity, preferably in the presence of a salt at a concentration exhibiting higher osmotic pressure than isotonic sodium chloride solution, to promote absorption of the medicine through a gastrointestinal organ such as colon or rectum, and through the vagina.

13 Claims, 8 Drawing Sheets

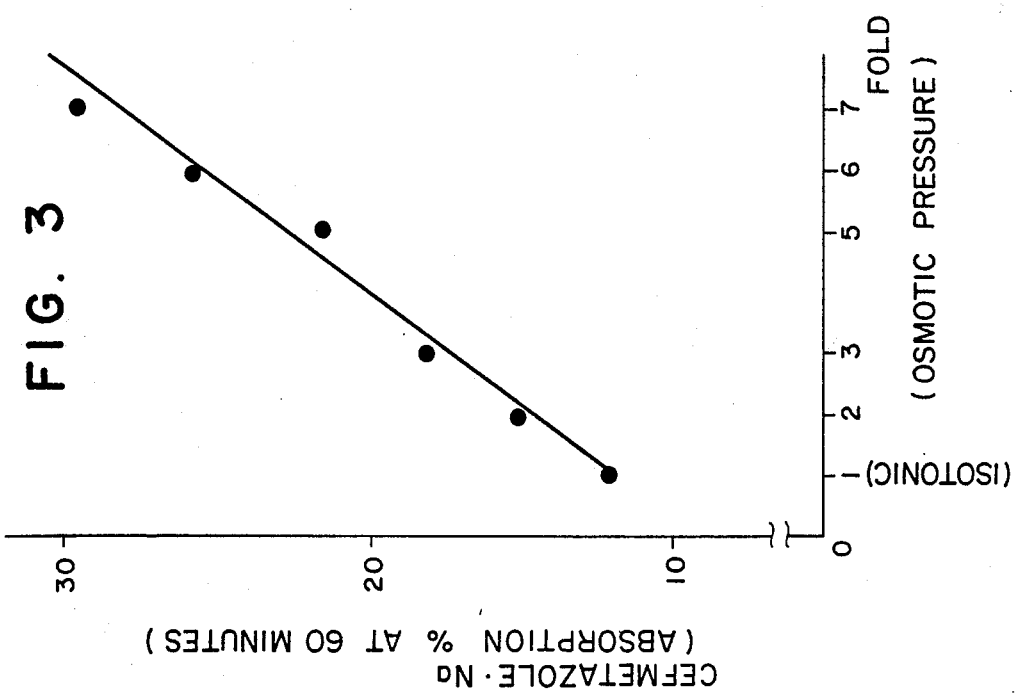
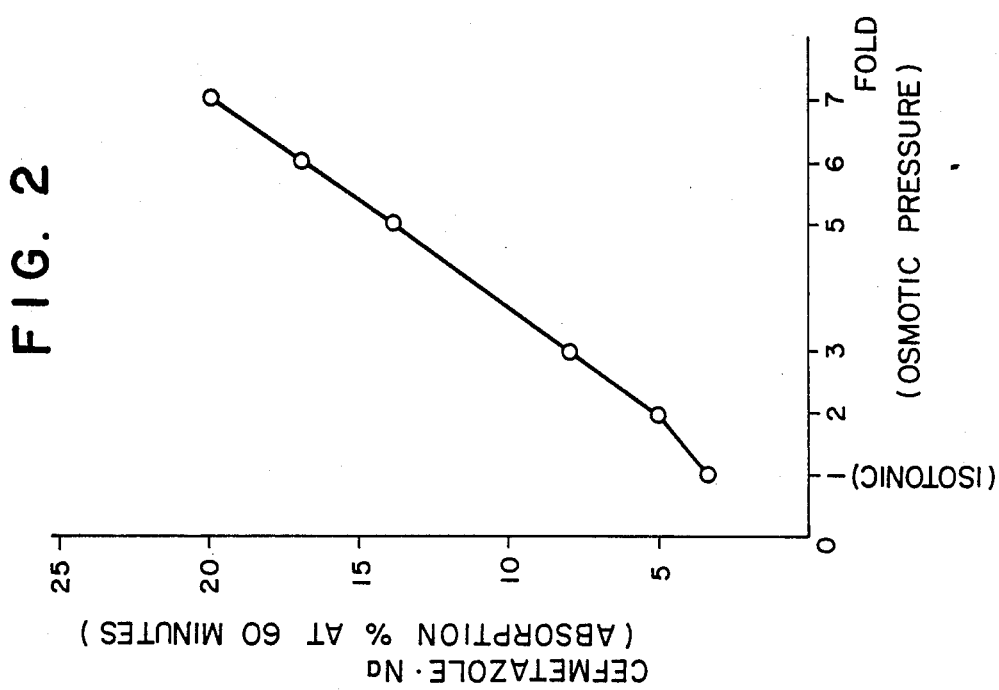

PREPARATION WHICH PROMOTES THE ABSORPTION OF PEPTIDES

This application is a continuation of application Ser. No. 628,317, filed July 6, 1984, which is a continuation-in-part of application Ser. No. 342,079, filed Jan. 25, 1982 both abandoned.

This invention relates to novel rectal compositions having excellent absorption property which are intended for improvement of absorption of medicines which are poor in absorption property through the rectum or other digestive organs in a body by administration of such a medicine simultaneously with a water-soluble substance exhibiting higher osmotic pressure than isotonic sodium chloride solution and a water-soluble compound having chelating action.

Absorption of a medicine through a digestive organ, irrespective of whether it may be stomach, small intestine, large intestine, rectum or mouth, has heretofore been generally believed to proceed according to pH Partition theory (Modern Pharmaceutics, Mercel Dekker, Inc., p. 31-49). Hence, a medicine readily dissociated in respective organs at absorption sites or a medicine having poor lipophilicity tends to be poorly absorbed. Such poorly absorptive medicines are administered as injections under the present circumstances. Various suggestions for improvement of absorption property of medicines have been made. These include, for example, Prodrug, Sofdrug, and utilization of ion pairs of complex formation. But none of these proposals is effective for all medicines, and no universally applicable method is known in the art.

It has now been found that in the mechanism of membrane absorption through digestive organs or the vagina, which is believed to proceed according to the pH Partition theory as mentioned above, a compound having a chelating action capable of bonding at least calcium ions or magnesium ions causes a change in membrane permeability, whereby membrane absorption of a medicine can be improved. It has also been found that membrane absorption can be markedly improved by addition of a water-soluble substance at a concentration exhibiting higher osmotic pressure than isotonic sodium chloride solution so that the preparation is absorbed under conditions of higher tonicity than the osmotic pressure of a body fluid. In addition to these findings, it has been found that a preparation obtained by use of vehicle, additives selected as desired and medicinal agent, for example, a suppository for insertion into the rectum or vagina is a good suppository from which the medicinal agent is excellently absorbed through membranes, thereby to maintain a high concentration of the medicine in blood for a long time. A large variety of pharmaceutical agents may be used in the present invention. Water soluble medicaments, for example, those with partition coefficients of 50 or less in chloroform/water or medicines readily dissociated into ions, are useful. Further, medicines previously thought to be applicable only as injections are also found to be excellently absorbed from preparations such as suppositories. Even medicines with high molecular weight such as polypeptide hormones are also found, in accordance with this invention, to be efficiently absorbable in the form of suppositories or similar preparations.

A principal object of the present invention is to provide compositions from which the absorption of medicinal agents can be improved.

In the accompanying drawings,

FIGS. 2, 3 and 4 are curves plotting percentages of disapperance of Cefmetazole.Na versus osmotic pressure, respectively;

Figure 1:
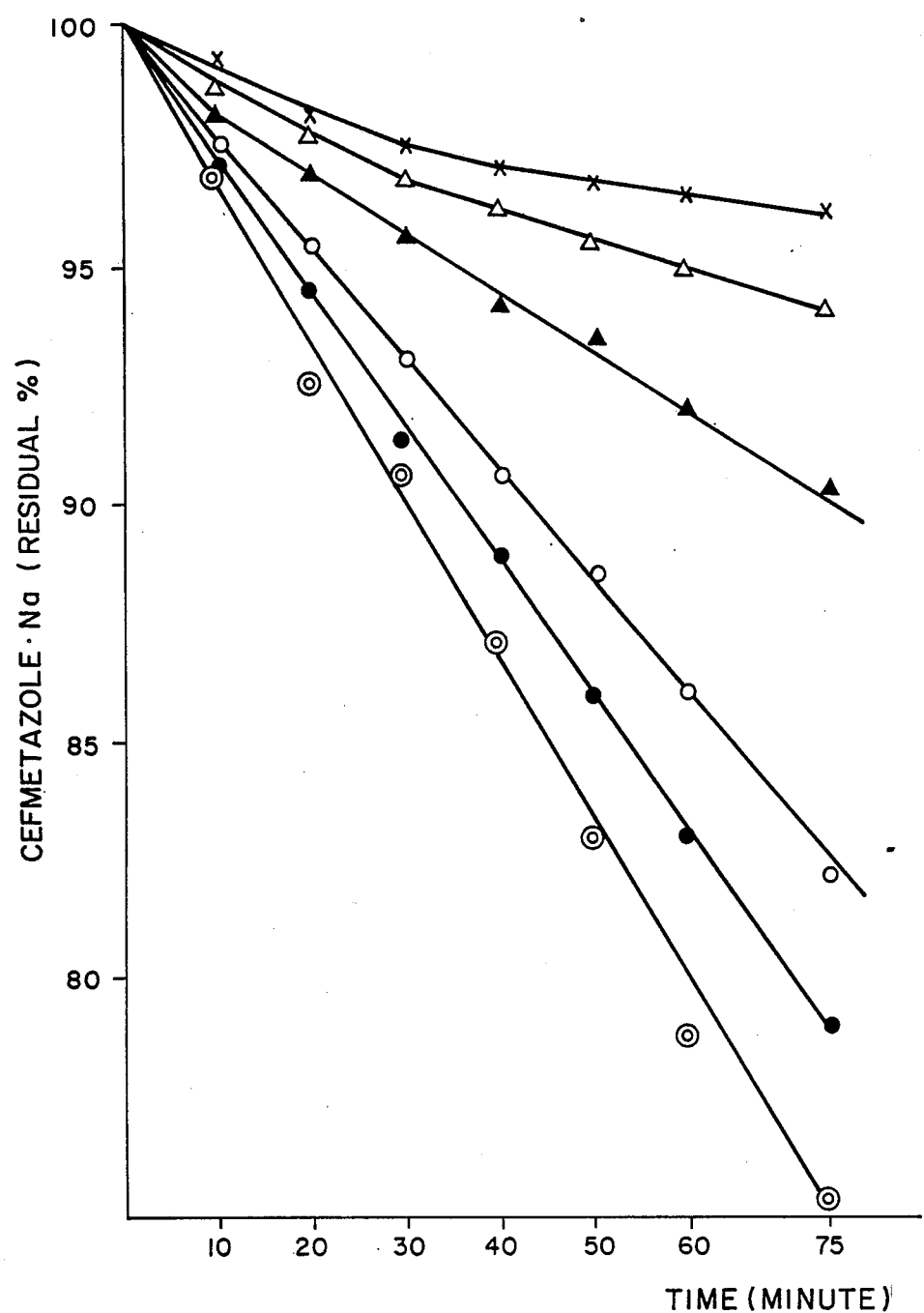
FIG. 1 shows disappearance curves for various osmotic pressures of Cefmetazole when using Cefmetazole.Na as medicine, in which the percentages of Cefmetazole which disappear by absorption are plotted versus measurement time.

According to the present invention, a preparation is provided which comprises an amount of a water-soluble substance which when dissolved in water or an aqueous media exhibits an osmotic pressure higher than isotonic sodium chloride solution, a water-soluble compound having chelating activity and a medicine.

The water-soluble substance used in the present invention at a concentration exhibiting higher osmotic pressure than isotonic sodium chloride solution may preferably be one which is chemically and therapeutically inert and can produce solutions with high osmotic pressure at very low concentrations. These include water-soluble salts and sugars.

The term "water-soluble" used in the specification of the present invention means the solubility of not more than 30 parts of water per one part of substance on the basis of the United States Pharmacoperia.

Sodium chloride is preferred since it is safe and readily and rapidly soluble in water to produce solutions of controlled osmotic pressure. Mannitol or glucose is preferred among water-soluble sugars. Generally speaking, water-soluble salts may include, for example, halides, sulfates, phosphates or carbonates of alkali metals such as sodium, potassium or lithium. More specifically, the aforesaid sodium chloride or sodium sulfate, disodium hydrogen phosphate, sodium dihydrogen phosphate, sodium phosphate, sodium hydrogen cabonate, sodium carbonate, potassium chloride, potassium sulfate, potassium hydrogen phosphate, potassium carbonate, lithium chloride, etc. These salts may be adjusted to concentrations exhibiting higher tonicity than the osmotic pressure of isotonic sodium chloride solution. For example, in case of sodium chloride, it may generally be adjusted to a concentration of 1 W/W % or higher. The upper limit of the concentration is not particularly limited, but preferably the concentration is about 2 to 30 W/W %. As preferable water-soluble sugars, there may be employed monosaccharides or disaccharides frequently used for adjustment of osmotic pressure in pharmaceutical technology, including, for example, glucose, mannitol, sorbitol, xylitol, lactose, maltose and sucrose. Such sugars may be used at concentrations with higher tonicity than isotonic sodium chloride solution, which is generally 0.25 M or higher. These water-soluble substances may be used in combination of two or more components for adjustment of osmotic pressure. The preferred osmotic pressure is 1.5 to 6 times the osmotic pressure exhibited by isotonic sodium chloride solution.

In connection with osmotic pressure, description is herein made by comparison with isotonic sodium chloride solution, but such a description with the use of isotonic sodium chloride solution as control is merely exemplary for comparison between osmotic pressures.

Reference is now made to compounds having chelating action for use in this invention. The mechanism of the absorption promotion effect has not so far been clarified, but it seems likely that the membrane absorption mechanism is changed through the chelating action and affinity to membrane possessed by these absorption promoters on the structures of cell membranes or the spaces between the epithelial cells to thereby promote absorption. At present, the mechanism of action of the absorption promoter for increase of membrane absorption through rectum or other is speculation. It is known, however, that compounds having chelating action capable of bonding to at least calcium ions or magnesium ions are useful typical chelating ligands for use in this invention and include, for example, acid groups such as the carboxylic acid, thiocarboxylic acid, sulfonic acid groups; or phosphoric acid groups; phenolic hydroxyl groups; or hydroxyl, imino, carbonyl, amino and similar groups. Further, as compounds having chelating action with these chelating ligands, there may be included organic compounds having at least one acid group together with another group to form the chelate ring. These include, for example, compounds having carbonyl groups, hydroxy- or amino-carboxylic-, iminocarboxylic-, sulfonic-, phosphoric-compounds having hydroxyl groups or amino groups and polyacid compounds having two or more caboxylic acid groups, sulfonic acid groups or phosphoric acid groups. These compounds may also be classified into respective groups of aliphatic compounds, alicyclic compounds, aromatic compounds and heterocyclic compounds. Further, keto-enol type tautomeric isomers may be classified either as compounds having carbonyl groups or as compounds having hydroxyl groups. To set forth examples of these groups, polyacid compounds may include oxalic acid, malonic acid, succinic acid, glutaric acid, maleic acid, glutonic acid, adipic acid, fumaric acid, aconitic acid, pimellic acid, sebacic acid, suberic acid, azelaic acid, acridinic acid, allylmalonic acid, mesaconic acid, brassylic acid, dodecanoic acid, methylmalonic acid, ehtylmalonic acid, phthalic acid, terephthalic acid, homophthalic acid, phenylsuccinic acid, phenylmalonic acid, phenylenediacetic acid, 1,3-naphthalenedicarboxylic acid, iminodiacetic acid, β-alaninediacetic acid, hydrochelidonic acid, 1,2-cyclohexanedicarboxylic acid, anthranylinoacetic acid, oxanylic acid-o-carboxylic acid, tricarballylic acid, 1,3-diaminopropanetetraacetic acid, hydroxyethyliminodiacetic acid, ethylenediaminediacetic acid, ethylenediaminedipropionic acid, hydroxyethylethylenediaminetriacetic acid, ethylenediaminetetraacetic acid, ethyleneglycol-bis(β-aminoethylether) N,N'-tetraacetic acid, trans-cyclohexanediaminetetraacetic acid, diaminopropanoltetraacetic acid, diethylenetriaminepentaacetic acid, ethylenediamine-di-o-hydroxyphenylacetic acid, triethylenetetraminehexaacetic acid, nitrilotriacetic acid, nitrilotripropionic acid and the like. Examples of hydroxy-acid compounds or phenolic hydroxyl group-acid compounds are lactic acid, citric acid, isocitric acid, malic acid, glycetic acid, tartaric acid, oxyacetic acid, dihydroxyethylglycinepantothenic acid, pantoic acid, mevalonic acid, iduronic acid, saccharic acid, phosphenolpyruvic acid, 2-phosphoglyceric acid, 3-phosphoglyceric acid, glycero-3-phosphoric acid, glucose-1,6-diphosphoric acid, fructose-1,6-diphosphoric acid, α-oxybutyric acid, β-oxybutyric acid, gluconic acid, α-oxyisobutyric acid, glucuronic acid, galaturonic acid, leusinic acid, oxyglutamic acid, diethooxalic acid, atrolactinic acid, phenyllactic acid, naphthylglyconic acid, phenylhydroacrylic acid, benzylic acid, mandelic acid, salicyclic acid, 2,5-dihydroxybenzoic acid, 2,3-dihydroxybenzoic acid, 2,6-dihydroxybenzoic acid, tetraoxyhexahydrobenzoic acid, shikimic acid, melilotic acid, hexahydrosalicylic acid, o-, m-, p-phenolsulfonic acid, 1,2-hydroxybenzene-3,5-disulfonic acid, 1-naphthol-2-sulfonic acid, 1-naphthol-3,6-disulfonic acid, 4-aminophenol-2-sulfonic acid, and the like. Exemplary carbonyl-acid compounds are glyoxalic acid, glyoxylylacetic acid, acetoacetic acid, oxaloacetic acid, α-ketobutyric acid, acetopyruvic acid, pyruvic acid, α-ketoglutaric acid, β-ketoglutaric acid, α-ketomalonic acid, α-ketovaleric acid, β-ketovaleric acid, benzoylformic acid, benzoylglycolic acid, benzoylpropionic acid, benzoylbutyric acid, levulinic acid, β-ketocapric acid, phenylpyruvic acid, oxanylic acid, and the like. Typical examples of monoacid compounds are butyric acid, isovaleric acid, caproic acid, caprylic acid, capric acid, undecylic acid, lauric acid, myrystic acid, palmitic acid, stearic acid, eicosanic acid, arachidonic acid, linoleic acid, linolenic acid, phenylthioacetic acid, phenylpropionic acid, α-phenylbutyric acid, acetylsalicylic acid, anisic acid, phenylphosphoric acid and the like. A compound containing phenolic hydroxyl groups may be, for example, salicylic acid as mentioned above. Aminoacid compounds may include amino acids such as quinaldic acid, kynurenic acid, glycine, alanine, proline, hydroxyproline, phenylalanine, phenylglycine, thyrosine, cystine, cysteic acid, ε-aminocaproic acid, aspartic acid, glutamine, glutamic acid, leusine, isoleusine, serine, valine, threonine, methionine, p-hydroxyphenylglycine, alginine, tryptophan, hystidine, lysine, γ-carboxyglutamic acid, kynurenine and the like. Further, as the organic compounds having at least two carbonyl groups, there may be preferably employed enamine derivatives between amino acids (e.g. glycine, lysine, leusine, serine, phenylalanine, glutamic acid, thyrosine, phenylglycine, p-hydroxyphenyl glycine, proline, hydroxyproline) and diketo compounds (e.g. acetylacetone, propionylacetone, butyroylacetone, 3-phenylacetylacetone, methylacetoacetate, ethylacetoacetate, ethyldiacetoacetate, propylacetoacetate, methoxyethylacetoacetate, ethoxyethylacetoacetate, diethyl ethoxymethylenemalonate, dibutyl ethoxymethylmalonate, etc.) In addition, the above diketo compounds per se can also be employed as absorption promoters. These absorption promoters are generally used in the form of alkali metal salts such as sodium salts or potassium salts, or ammonium salts, but they may also be esterified to the extent such that water-solubility is not impaired. In some of absorption promoters, for example, polyacid compounds such as ethylenediaminetetraacetic acid (EDTA) or ethyleneglycol-bis($\beta$-amino-ethyl ether)-N,N'-tetraacetic acid (EGTA), a part of the acid groups may be protected by esterification etc. to be converted to derivatives. In particular, in case of EDTA, one of the carboxylic groups may be converted to ethylester to obtain a derivative having better effect of promoting absorption of a medicine.

The watersoluble compound and the compound having chelating action may be employed in amounts of 0.05 W/W % or more, generally in the range of from 0.1 to 50 W/W %, preferably from 1.0 to 30 W/W %. As the vehicle to be employed for preparation of a suppository containing the above absorption promoter, a medicine and preferably a water-soluble salt to be added for increase of tonicity, there may suitably be selected one from oily vehicles and water-soluble vehicles conventionally used in preparation of suppositories of rectal injections, and a surfactant may also be added if desired.

As these oily vehicles or water-soluble vehicles, there may conveniently be used those as described in "The Theory and Practice of Industrial Pharmacy", p. 245 to 269 (1976).

The medicine to be used in the present invention is not particularly limited, but there may be employed ordinary pharmaceuticals, water-soluble medicines are particularly preferred, especially those with a partition coefficient of 50 or less in chloroform/water. Medicines readily dissociated to ions are also useful. For example, there may be included various medicines such as hypnotics, tranquilizers, antiepileptics, antipyretics, antalgics, antidepressants, muscle relaxants, antiinflammatory agents, antiallergic agents, immunosuppressants, antirheumatics, vasodilators, antihemorrhage agents, antihypertensives, antibiotics, antibacterial agents, urinary tract sterilizers, anti-tumor agents, vitamins, hormones and galenicals. More specifically, typical examples are penicillin type antibiotics such as ampicillin, hetacillin, amoxicillin, cyclacillin, cloxacillin, dicloxacillin, oxacillin, carindacillin, sulbenicillin, piperacillin, apalcillin, methicillin, etc. or combined drugs of ampicillin or amoxicillin with oxacillin, cloxacillin, floxacillin or dicloxacillin or carbenicillin; cephalosporin ($\beta$-lactam) type antibiotics such as cephalothin, cephazolin, cephaloridine, cephacetorile, cefoxitin, cefadroxil, cefatrizine, cephaloglycin, cephalexin, cephapirin, cephaclor, ceftezol, cefuroxime, cefsulodin, cefmetazole, etc. and non-toxic salts thereof such as alkali metal salts (e.g. sodium salts or potassium salts), ammonium salts or benzylamine salts. In addition, there may also be mentioned tetracycline type antibiotics such as doxycycline, oxycycline, etc; aminosaccharide type antibiotics such as kanamycin, sisomicin, amikacin, tobramycin, netromycin, gentamycin, HAPA-B, etc.; peptide type antibiotics such as tuberactinomycin N, actinomycin, colistin, etc. or non-toxic salts thereof; further peptide hormones such as insulin, somatostatin, calcitonin, angiotensin, kallikrein, secretin, gastrisin, parathyroid hormone, enzyme such as lysozyme, orgotein, etc.; physiological active protein etc. Other medicines which may be employed include those such as barbital, theophylline, aspirin, mizoribine (bredinin), 5-fluorouracil; nucleic acid type antitumor agent such as neplanocin-A, neplanocin-C, Ara-C, Ara-A, heparin, methotrexate, L-dopa, etc.

The medicine may be employed in an amount, which may be selected and designed to be effective for its intended purpose. For example, in case of antibiotics such as $\beta$-lactam antibiotics 20 to 500 mg activity, generally 100 to 300mg activity, or in case of peptide hormones such as insulin, 1 to 500 units may be contained per gram of preparation. In general, the medicine may preferably be used in finely divided particles with 1 to 50 $\mu$ diameters or as an aqueous solution.

The preparations may be produced according to conventional methods for production of preparations in general such as rectal suppository, urethral suppository or vaginal suppository, ointments or creams. For example, the absorption promoter selected, a water-soluble substance in an amount exhibiting higher osmotic pressure than isotonic sodium chloride solution and a medicine are added to a vehicle, optionally in combination with a surfactant, and these components are thoroughly mixed to provide preparations.

Further, in production of these preparation, there may also be added preservatives such as methyl- or propyl-p-oxybenzoate, colorants, aromas and stabilizers.

The present invention is further illustrated in detail by referring to the following non-limiting Examples.

EXAMPLE 1

Absorption effects under conditions with various tonicities were examined. Each sample solution was prepared by adding 0.1 W/W % Cefmetazole.Na as medicine together with sodium oxalate or sodium glyoxalate as absorption promoter to a phosphate buffer of pH 7.0 conditioned with sodium chloride to a tonicity which is varied from isotonic up to seven fold tonicity.

The experiment was conducted in the following manner. Sprague Dawley rats (male), weighing 200 to 300 g, were narcotized (after fast for 20 hours) with pentobarbital (50 mg/kg) and thereafter subjected to hypoabdominal incision for a first cannulation at a position about 1.5 cm from anus and also another cannulation at a position 5 cm above the first cannulation. Subsequently, the rectum was internally washed with about 50 ml of isotonic sodium chloride solution kept at 38° C., and samples each of 10 ml were circulated through rectum for 5 minutes (2 ml/minute) to make the concentration in the system constant. Then, 5 ml of each sample was circulated at a flow rate of 2 ml/minute, and samples each of 0.05 ml were collected at intervals of 10 minutes from 0 minute. Each sample was diluted to 5 ml with distilled water and the quantity of medicine disappeared by absorption was determined by UV spectrophotometer.

As the result, the disappearance curve of Cefmetazole.Na under the condition of 0.1 W/W % sodium oxalate was obtained as shown in FIG. 1, in which x—x shows the result under the isotonic condition, △—△ under two-fold tonicity, ▲ — ▲ under three-fold tonicity, ○ — ○ under five-fold tonicity, ● — ● under six-fold tonicity and ⊙—⊙ under seven-fold tonicity.

FIG. 2 also shows the absorption curve of Cefmetazole.Na under the above condition of 0.1 W/W % sodium oxalate at respective osmotic pressures.

FIG. 3 shows the absorption curve of Cefmetazole.Na under the condition of 0.2 W/W % sodium oxalate at respective osmotic pressures.

Figure 4:
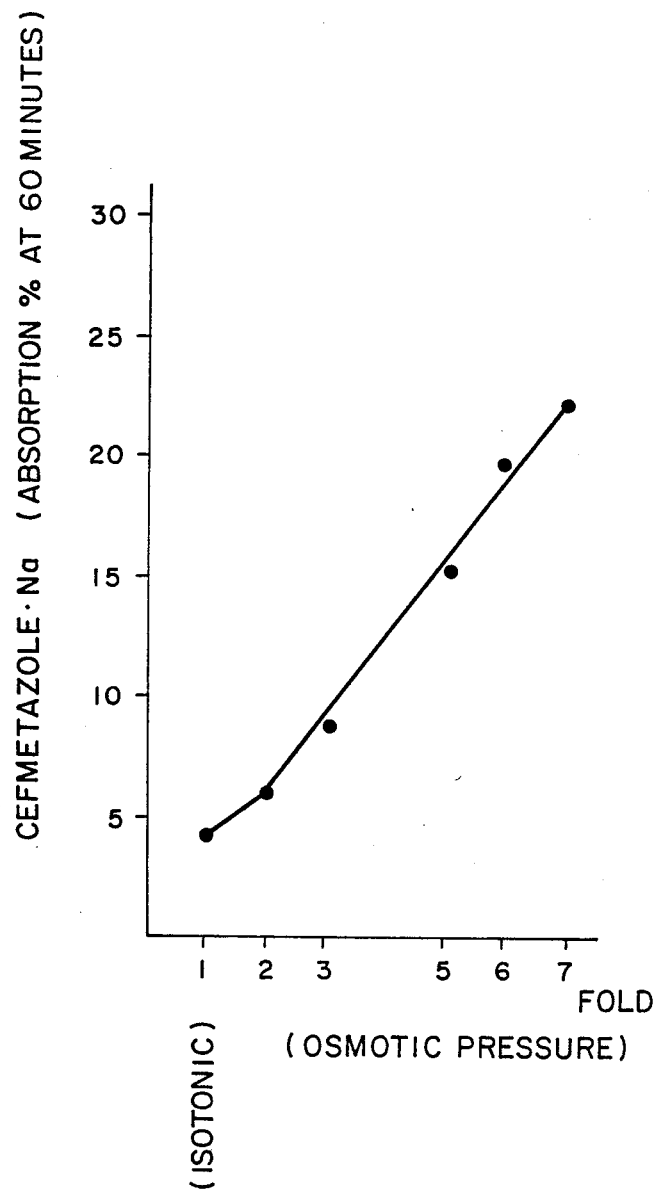

Further, FIG. 4 shows the absorption curve of Cefmetazole.Na under the condition of 0.5 W/W % sodium glyoxalate at respective osmotic pressures.

EXAMPLE 2

Using 0.1 W/W % Cefoxitin.Na as medicine and 0.5 W/W % of sodium glyoxalate as absorption promoter under respective osmotic pressure conditions (namely two-fold, four-fold and six-fold tonicities with the use of sodium chloride) and following otherwise the same procedure as in Example 1, quantities of Cefoxitin disappeared by absorption were determined by UV-spectrophotometer similarly as in Example 1.

Figure 5:
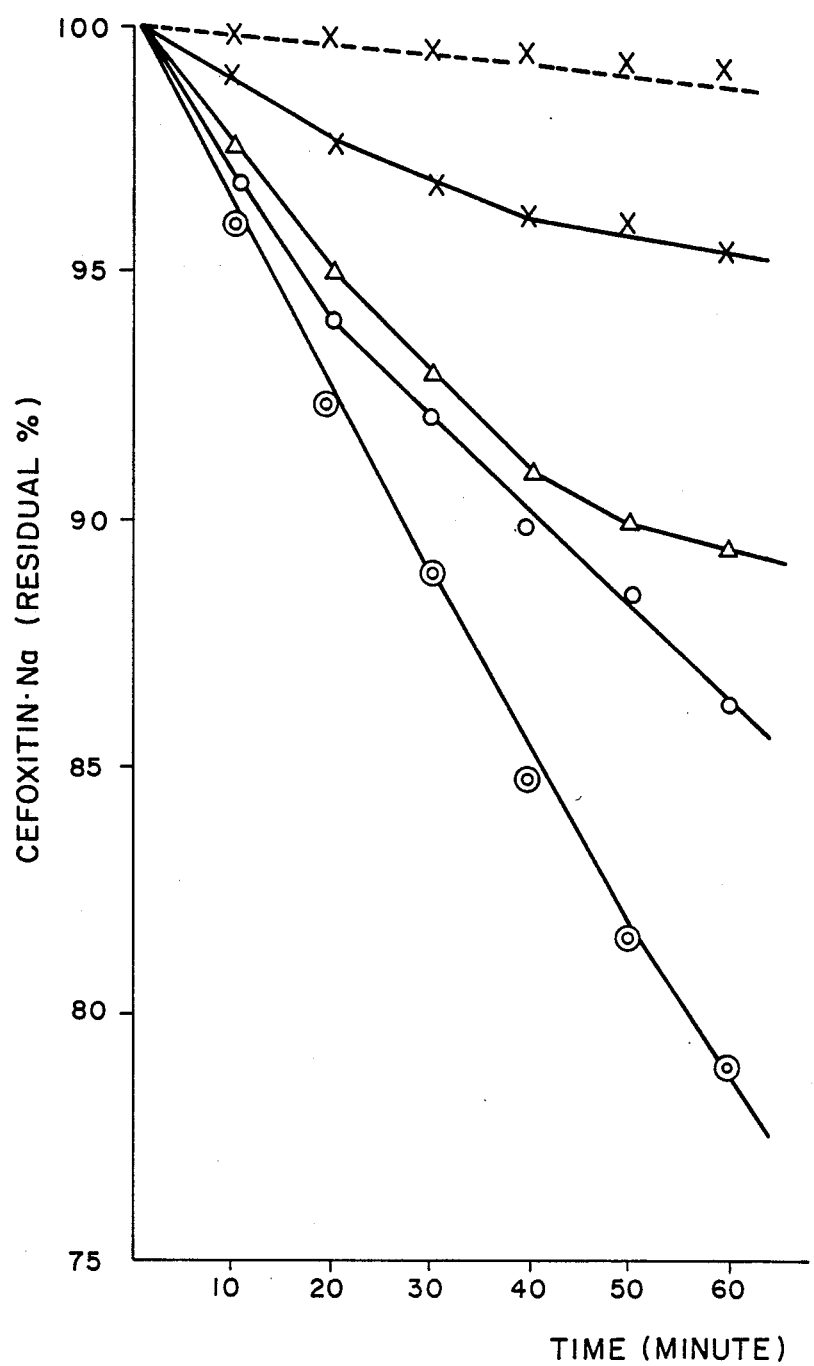
FIG. 5 is a disappearance curve of Cefoxitin.Na versus osmotic pressure.

The results are shown in FIG. 5, in which x—x is the disappearance curve by absorption only of Cefoxitin under isotonic condition without use of sodium glyoxalate, x—x the disappearance curve of Cefoxitin with the use of sodium glyoxalate under isotonic condition, ○ — ○ that under two-fold tonic condition, △ — △ that under four-fold tonic condition, and ● — ● that under six-fold tonic condition, respectively.

EXAMPLE 3

Quantities of 0.5 W/W % Cefmetazole.Na disappeared by absorption under isotonic and three-fold tonic conditions were determined, respectively, using sodium malate, sodium pyruvate, sodium phosphenolpyruvate, sodium β-hydroxybutyrate, sodium β-hydroxy glutarate, and sodium 2-phospho-D-glycerate. The results are shown in Table 1.

TABLE 1

| (Values after 60 minutes) | Isotonic condition | Three-fold tonic condition |
|---|---|---|
| Sodium malate | 4.9% | 10.2% |
| Sodium pyruvate | 5.2% | 10.9% |
| Sodium phosphenolpyruvate | 7.3% | 16.6% |
| Sodium β-oxybutyrate | 6.6% | 14.0% |
| Sodium β-oxyglutarate | 7.8% | 16.5% |
| Sodium 2-phospho-D-glycerate | 5.4% | 13.8% |

When no absorption promoter was employed, the quantity of 0.1 W/W % Cefmetazole.Na disappeared by absorption under isotonic condition was practically negligible.

EXAMPLE 4

Figure 6:
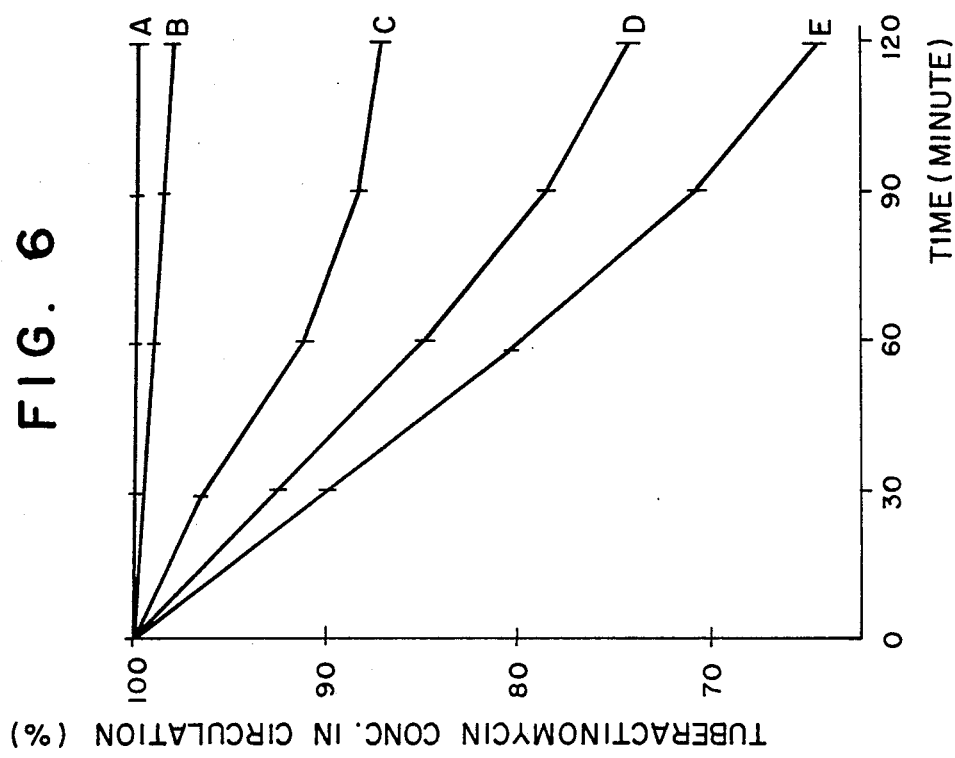
FIG. 6 shows disappearance curves of respective samples (A, B, C, D and E) in Example 4.

Using 0.01% solution of Tuberactinomycin, rectum circulation experiments were conducted in the same manner as in Example 1, and the Tuberactinomycin concentrations in the Perfusates were determined by measurement of antimicrobial activities (according to Japanese antimicrobial standards) with lapse of time. As the result, absorptions through rectum were found to be increased by the presence of EDTA.2Na and sodium chloride, as shown in FIG. 6.

Sample A (Control):
  0.01% Tuberactinomycin
  0.9% sodium chloride
Sample B (Control):
  0.01% Tuberactinomycin
  5% sodium chloride
Sample C (Present invention):
  0.01% Tuberactinomycin
  5% sodium chloride
  0.05% EDTA disodium salt
Sample D (Present invention):
  0.01% Tuberactinomycin
  5% sodium chloride
  0.1% EDTA disodium salt
Sample E (Present invention):
  0.01% Tuberactinomycin
  5% sodium chloride
  1% EDTA disodium salt.
(Each sample was dissolved in 0.1M Tris-HCl buffer and adjusted to pH 7.5.)

EXAMPLE 5

Using 1% solution of Tuberactinomycin (in 0.1M Tris-HCl buffer, pH 7.5) as Control, an injection agent was prepared by adding 5% sodium chloride and 1.0% EDTA disodium salt to said solution. Each 0.5 ml of these samples was injected into rat through anus and the concentration of Tuberactinomycin in blood was measured to find that it appeared in blood at concentrations shown below.

| | Concentration in blood ($\gamma$/ml) | | | | | |
|---|---|---|---|---|---|---|
| | 10 min. | 20 min. | 30 min. | 45 min. | 60 min. | 90 min. |
| Control: | lower than measurable limit of antimicrobial activity | | | | | |
| Present invention: | 5$\gamma$ | 10$\gamma$ | 11$\gamma$ | 8$\gamma$ | 7$\gamma$ | 2$\gamma$ |

EXAMPLE 6

Using 2% solution of Cephalothin.Na (in 0.1M Tris-HCl buffer, pH 8.0) as Control, an injection agent was prepared by adding 6% sodium chloride and 1.0% disodium EDTA mono-ethylate to said solution. Each 0.5 ml of these samples was injected into rat through anus, and concentrations of Cephalothin in blood were determined by measurement of antimicrobial activities (according to Japanese antimicrobial standards) to find that the concentrations in blood were significantly increased.

| | Concentration in blood ($\gamma$/ml) | | | | | |
|---|---|---|---|---|---|---|
| | 10 min. | 20 min. | 30 min. | 45 min. | 60 min. | 90 min. |
| Control: | — | ± | <1$\gamma$ | <1$\gamma$ | — | — |
| Present invention: | 8$\gamma$ | 12$\gamma$ | 14$\gamma$ | 5$\gamma$ | 3$\gamma$ | — |

EXAMPLE 7

Figure 7:
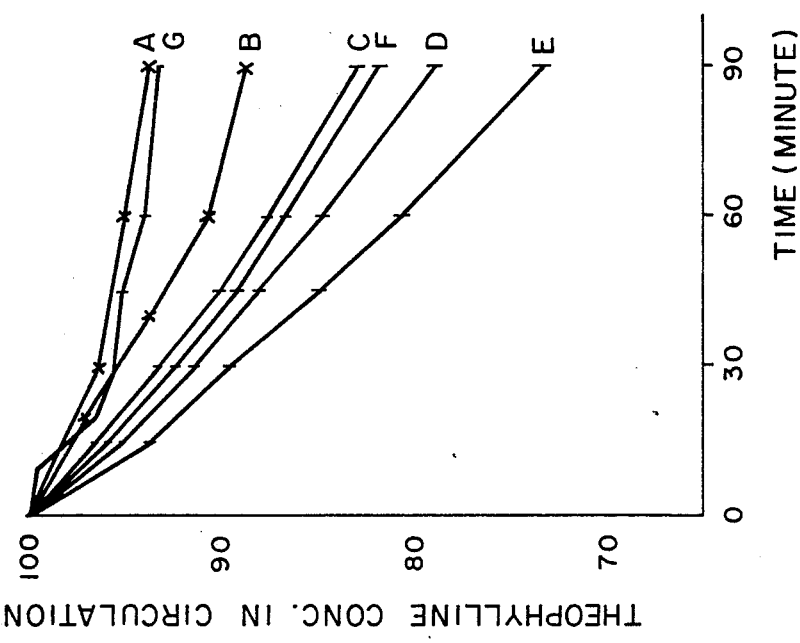
FIG. 7 shows disappearance curves of samples A, B, C, D, E, F and G in Example 7.

Using 0.04% solution of Theophylline (in 0.1M Tris-HCl buffer, pH 8.0), concentrations of circulated fluids were measured by UV absorption ($\lambda_{max}$=270 nm) with lapse of time as in Example 1, whereby absorption by rectum was found to be increased by the presence of EDTA.2Na and sodium chloride as shown in FIG. 7.

A (Control):
  0.04% Theophylline
  0.9% sodium chloride
B (Control):
  0.04% Theophylline
  0.1% EDTA disodium salt
  0.8% sodium chloride
C (Prevent invention):
  0.04% Theophylline
  0.1% EDTA disodium salt
  2% sodium chloride
D (Present invention):
  0.04% Theophylline
  0.1% EDTA disodium salt
  4% sodium chloride E (present invention):
  0.04% Theophylline
  0.1% EDTA disodium salt
  8% sodium chloride
F (Present invention):
  0.04% Theophylline
  1.0% EDTA disodium salt
  4% sodium chloride
G (Present invention):
  0.04% Theophylline
  4.0% EDTA disodium salt
  4% sodium chloride.
(Each sample was dissolved in 0.1M Tris-HCl buffer and the pH was adjusted to 8.0.)

EXAMPLE 8

An intrarectal injection preparation was obtained by adding calcitonin (CT: 625 mu/ml) based on the total amount; 25 ng/0.2 ml), sodium oxalate (0.2 W/W % based on the total amount) and glucose (isotonic; 0.25M, three-fold tonic; 0.75M, six-fold tonic; 1.5M) to a base of carboxyvinyl polymer (CVP: Wako Gel 105, produced by Wako Jyunyaku Co., Ltd.) and 0.2 ml of this preparation was injected into rats (SD rats, four weeks of age). Calcium concentration after one hour was measured, and the relative effects were evaluated as compared with calcium concentration by CVP and CT which was set at standard value of 1. The results are shown in Table 1.

TABLE 2

| Medicine | Isotonic | 3-fold tonic | 6-fold tonic |
|---|---|---|---|
| CT | 1 | 1.05 | 1.67 |
| CT + sodium oxalate | 5.4 | 6.9 | 10.9 |

EXAMPLE 9

Suppositories having the following compositions were inserted through anus into six male beagle dogs, weighing 9.5 to 10.5 kg, and concentrations in blood were measured 15 minutes, 30 minutes, 60 minutes, 120 minutes and 180 minutes after administration to obtain the results as shown in Table 3.
Control: Suppository comprising 100 mg activity of Tuberactinomycin N.sulfate pulverized to 50 microns or less and 400 mg of cacao butter
Present invention: Suppository comprising 100 mg activity of Tuberactinomycin N.sulfate, 50 mg of sodium chloride, 10 mg of EDTA.2Na and 180 mg of cacao butter

TABLE 3

| | Beagledog No. | Concentration in blood (γ/ml) | | | | |
|---|---|---|---|---|---|---|
| | | 15 min. | 30 min. | 60 min. | 120 min. | 180 min. |
| Control | 1 | — | 0.8 | 0 | — | — |
| | 2 | 1.0 | 2.3 | 1.3 | — | — |
| | 3 | — | 1.5 | — | — | — |
| | 4 | — | 0.9 | 0.7 | — | — |
| | 5 | — | — | — | — | — |
| | 6 | — | — | — | — | — |
| Present invention | 1 | 3.9 | 12.0 | 7.6 | 4.2 | 2.2 |
| | 2 | 9.7 | 11.7 | 5.4 | 3.5 | 2.7 |
| | 3 | 9.2 | 10.0 | 8.1 | 4.8 | 3.0 |
| | 4 | 5.6 | 7.7 | 7.4 | 3.2 | 1.9 |
| | 5 | 10.8 | 9.2 | 7.3 | 6.0 | 2.0 |
| | 6 | 6.9 | 11.4 | 9.3 | 7.7 | 4.4 |

EXAMPLE 10

As the group of polycarboxylic acid compounds (aliphatic compounds), there were employed sodium oxalate, malonic acid, maleic acid, fumaric acid, adipic acid, glutaric acid, pimellic acid, EDTA.2Na, trans-cyclohexanediaminetetraacetic acid (CyDTA), iminodiacetic acid, nitrilotriacetic acid, ethylmalonic acid, trans-aconitic acid, diaminopropanoltetraacetic acid (DTPA-OH), each at a concentration of 0.1% W/V, and the quantities of Cephalothin disappeared by absorption were determined one hour after administration of 0.1% W/V Cephalothin.Na under isotonic (×1), two-fold tonic (×2) and four-fold tonic conditions (×4), respectively. The experiments were conducted similarly as in Example 1. That is, Wistar-strain male rats, weighing 250 to 300 g, were narcotized with pentobarbital (50 mg/kg) and thereafter subjected to hypoabdominal incision for a first cannulation at a position about 1.5 cm from anus and also another cannulation at a position 5 cm upper than said first cannulation. Subsequently, rectum was internally washed with about 20 ml of isotonic sodium chloride solution kept at 38° C., and each sample was circulated at a flow rate of 2 ml/minute for 5 minutes to make the concentration in the system constant. Then, 6 ml of each sample was circulated at a flow rate of 2 ml/minute, and samples each of 0.05 ml were collected at intervals of 10 minutes. Each sample was diluted and the quantity of Cephalothin disappeared was determined by UV-spectrophotometer of high-speed liquid chromatography.

The results of Cephalothin disappeared when collecting respective samples after one hour are shown below in Table 4.

TABLE 4

| Group of polycarboxylic acids (aliphatic compounds) | Osmotic pressure (%) | | |
|---|---|---|---|
| | ×1 | ×2 | ×4 |
| No addition | 1.2 | 1.6 | 3.1 |
| Sodium oxalate | 6.6 | 11.1 | 18.3 |
| Malonic acid | 4.5 | — | 13.0 |
| Succinic acid | 8.2 | 13.1 | 24.0 |
| Maleic acid | 6.3 | 10.6 | 18.3 |
| Fumaric acid | 5.5 | — | 17.3 |
| Adipic acid | 7.5 | 11.2 | 20.0 |
| Glutaric acid | 5.7 | 9.3 | 15.2 |
| Pimellic acid | 5.1 | 7.8 | 15.0 |
| EDTA · 2Na | 9.4 | 17.1 | 31.2 |
| CyDTA | 8.1 | 15.0 | 32.3 |
| Iminodiacetic acid | 7.1 | 14.2 | 17.0 |
| Nitrilotriacetic acid | 4.4 | — | 10.4 |
| DTPA-OH | 7.5 | 13.7 | 21.6 |
| Trans-aconitic acid | 10.5 | 18.6 | 27.8 |
| Ethylmalonic acid | 12.3 | 24.2 | 36.9 |

EXAMPLE 11

As the group of aliphatic keto-carboxylic acid compounds, there were employed sodium glyoxalate, sodium pyruvate, sodium ketomalonate, sodium α-ketoglutarate, sodium oxaloacetate, α-ketobutyric acid, α-ketovuleric acid and levulinic acid each at a concentration of 0.1% W/V and the quantities of Cephalothin disappeared by absorption were determined one hour after administration of 0.1% W/V Cephalothin.Na under isotonic (×1), two-fold tonic (×2) and four-fold tonic conditions, respectively. The results are shown in Table 5. (The experimental method was the same as in Example 10, and units in Table are percents.)

TABLE 5

| Group of aliphatic keto-carboxylic acids | Osmotic pressure (%) | | |
|---|---|---|---|
| | X 1 | X 2 | X 4 |
| Sodium glyoxalate | 4.9 | — | 13.1 |
| Sodium pyruvate | 7.0 | 11.6 | 23.1 |
| Sodium ketomalonate | 8.4 | 12.7 | 19.6 |
| α-ketoglutaric acid | 7.1 | — | 25.6 |
| Sodium oxaloacetate | 13.8 | 17.5 | 22.2 |
| α-ketobutyric acid | 11.2 | 18.3 | 30.9 |
| α-ketovaleric acid | 9.8 | 14.7 | 23.2 |
| Levulinic acid | 11.9 | 21.1 | 34.3 |
| No addition | 1.2 | 1.6 | 3.1 |

EXAMPLE 12

Using citric acid, malic acid, lactic acid, glucuronic acid and galacturonic acid as the group of aliphatic hydroxy-carboxylic acid compounds each at a concentration of 0.1 W/V %, quantities of Cephalothin disappeared by absorption were determined one hour after administration of 0.1 W/V % Cephalothin.Na under isotonic (X1), two-fold tonic (X2) and four-fold tonic (X4) conditions, respectively. The results are shown in Table 6. (The experiment method was the same as in Example 10, and units in the Table are percents.)

TABLE 6

| Group of aliphatic hydroxy-carboxylic acid compounds | Osmotic pressure | | |
|---|---|---|---|
| | X 1 | X 2 | X 4 |
| Citric acid | 4.5 | — | 11.3 |
| Malic acid | 7.2 | 12.3 | 18.8 |
| Lactic acid | 4.3 | — | 13.5 |
| Glucronic acid | 5.5 | 11.1 | 16.4 |
| Galactronic acid | 5.8 | 10.5 | 16.1 |
| No addition | 1.2 | 1.6 | 3.1 |

EXAMPLE 13

Using as the group of aromatic carobxylic acids, sodium salicylate, sodium sulfosalicylate, sodium phthalate and 2,6-dihydroxybenzoic acid, each at a concentration of 0.5 W/V %, quantities of Cephalothin.Na disappeared by absorption were determined one hour after administration of 0.1 W/V % Cephalothin.Na under isotonic (X1), two-fold tonic (X2) and four-fold tonic (X4) conditions, respectively. The results are shown in Table 7. (The experiment method was the same as in Example 10, and the units in the Table are percents.)

TABLE 7

| group of aromatic carboxylic acid compounds | Osmotic pressure | | |
|---|---|---|---|
| | X 1 | X 2 | X 4 |
| Sodium salicylate | 8.9 | 16.5 | 29.8 |
| Sodium sulfosalicylate | 10.4 | — | 19.7 |
| Sodium phthalate | 7.1 | — | 18.9 |
| 2,6-dihydroxybenzoic acid | 9.5 | 15.3 | 22.9 |

EXAMPLE 14

As the group of aromatic sulfonic acid compounds, 1,2-dihydroxybenzene-3,5-disulfonic acid (DHBDS) and 1-naphthol-3,6-disulfonic acid (NDS) were employed, each at a concentration of 0.1 W/V %, and the experiments were performed similarly as in Example 10. The results are shown in Table 8, wherein the units are percents.

TABLE 8

| Group of aromatic sulfonic acid compounds | Osmotic pressure | | |
|---|---|---|---|
| | X 1 | X 2 | X 4 |
| DHBDS | 9.8 | — | 22.0 |
| NDS | 12.6 | 19.8 | 31.6 |

EXAMPLE 15

Example 1 was repeated except that butyric acid, isovaleric acid, sodium caproate, sodium caprylate, sodium caprate and sodium laurate were employed as aliphatic carboxylic acid compounds, each at a concentration of 0.1 W/V %, to obtain the results as shown in Table 9. (The units in the Table are percents.)

TABLE 9

| Fatty acids | Osmotic pressure | | |
|---|---|---|---|
| | X 1 | X 2 | X 4 |
| Butyric acid | 9.9 | 17.1 | 21.0 |
| Isovaleric acid | 7.7 | — | 14.4 |
| Sodium caproate | 10.4 | 14.7 | 17.2 |
| Sodium caprylate | 5.8 | — | 13.0 |
| Sodium caprate | 5.2 | — | 8.6 |
| Sodium laurate | 3.9 | — | 6.5 |

EXAMPLE 16

Example 10 was repeated except that the aliphatic carboxylic compounds were replaced with ethylacetoacetate and 3-phenylacetyl acetone as diketo-compounds to obtain the results as shown in Table 10, wherein the units are percents.

TABLE 10

| Group of diketo-compounds | Osmotic pressure | | |
|---|---|---|---|
| | X 1 | X 2 | X 4 |
| Ethylacetoacetate | 14.6 | 20.2 | 26.7 |
| 3-Phenylacetyl acetone | 9.1 | 16.3 | 22.2 |

EXAMPLE 17

Example 10 was repeated except that the aliphatic carboxylic acid compounds were replaced with the group of amino-carboxylic acid compounds and imino-carboxylic acid compounds of DL-glycine DL-hydroxyproline (each at 0.5% W/V), DL-phenylalanine, DL-phenylglycine, N-phenylglycine, D1-aspartic acid, DL-glutamic acid, α-methyl D1-glutamate, DL-cysteic acid, ε-aminocaproic acid, N-dimethylphenylalanine, γ-carboxyglutamic acid, glycyl-DL-aminobutyric acid, glycyl-DL-aspartic acid (each at 0.1% W/V). The results are shown in Table 11, wherein the units are percents.

TABLE 11

| Group of amino-carboxylic acid and iminocarboxylic acid compounds | Osmotic pressure | | |
|---|---|---|---|
| | X 1 | X 2 | X 4 |
| DL-glycine | 6.9 | 9.4 | 14.0 |
| DL-hydroxyproline | 5.5 | — | 12.9 |
| DL-phenylalanine | 6.6 | — | 15.6 |
| DL-phenylglycine | 11.5 | 19.8 | 29.3 |
| N—phenylglycine | 12.0 | 22.3 | 30.8 |
| DL-aspartic acid | 11.6 | 15.6 | 22.4 |
| DL-glutamic acid | 12.1 | — | 22.3 |
| α-methyl DL-glutamate | 11.9 | — | 21.4 |
| DL-cysteic acid | 5.3 | 9.0 | 14.6 |
| ε-aminocaproic acid | 7.1 | 11.8 | 17.0 |
| N—dimethylphenylalanine | 10.9 | — | 25.5 |
| γ-carboxyglutamic acid | 13.1 | 24.6 | 31.4 |
| Glycyl-DL-aminobutyric acid | 11.0 | — | 30.4 |

TABLE 11-continued

| Group of amino-carboxylic acid and iminocarboxylic acid compounds | Osmotic pressure | | |
|---|---|---|---|
| | X 1 | X 2 | X 4 |
| Glycyl-DL-aspartic acid | 8.6 | — | 19.0 |

EXAMPLE 18

Example 10 was repeated except that as other acid compounds glycero-3-phosphoric acid, fructose-1,6-diphosphoric acid and ethylenediaminetetrakis(methylenephosphonicacid) (EDTPO) were used each at 0.1 W/V% in place of the aliphatic carboxylic acid compounds. The results are shown in Table 12, wherein the units are percents.

TABLE 12

| Acid compounds | Osmotic pressure | | |
|---|---|---|---|
| | X 1 | X 2 | X 4 |
| Glycero-3-phosphoric acid | 4.0 | — | 11.5 |
| Fructose-1,6-diphosphoric acid | 4.1 | 7.5 | 13.3 |
| EDTPO | 7.6 | — | 20.0 |

EXAMPLE 19

Cephalothin.Na(1 g activity) as medicine, α-ketoglutaric acid.Na (1 g) as absorption promoter and sodium chloride (500 mg) as hypertonicator were each pulverized and mixed together. A homogeneous dispersion was prepared by adding to the resulting mixture a base of Witepsol H-15 previously melted by fusion to a total amount of 10 g. The dispersion was intrarectally administered at a dose of 50 mg/kg to Wistar-strain rats (male, weighing 250 to 300 g, four per one group) and blood sampling was performed 15 minutes, 30 minutes, 60 minutes and 120 minutes after administration for measurement of Cephalothin concentration in serum (according to the bioassay using *Bacillus subtilis* ATCC 6633). As Controls, there were also obtained a preparation containing sodium chloride without use of the absorption promoter (Control 1) and a preparation containing the absorption promoter without use of sodium chloride (Control 2). Further, another preparation of this invention was also prepared by use of 1 g of α-ketobutyric acid in place of the above absorption promoter, following otherwise the same procedure as described above.

As the result, Cephalothin concentrations for respective preparations were found as listed in Table 13.

TABLE 13

| Preparation | Concentration in blood (γ/ml) | | | |
|---|---|---|---|---|
| | 15 min. | 30 min. | 60 min. | 120 min. |
| Control 1 (sodium chloride) | 0.2 | 0.5 | — | — |
| Control 2 (α-ketoglutaric acid · Na) | 2.1 | 5.3 | 1.2 | 0.3 |
| Present invention (α-ketoglutaric acid · Na/ sodium chloride) | 5.9 | 11.4 | 3.1 | 1.2 |
| Present invention (α-ketobutyric acid/ sodium chloride) | 7.9 | 13.0 | 4.5 | 1.4 |

EXAMPLE 20

Tuberactinomycin N.sulfate (1 g activity) as medicine, D-phenylglycine as absorption promoter (1 g) and sodium chloride as hypertonicator (500 mg) were each pulverized and thoroughly mixed. To the resulting mixture, there was added Witepsol H-15 previously melted by heating, followed by homogeneous dispersion, to provide a suppository for intrarectal administration. Example 19 was also repeated except that L-aspartic acid (1 g) was used in place of D-phenylglycine to obtain a suppository for intrarectal administration.

As Control, a preparation with the same composition as the above preparation except for containing no absorption promoter was also prepared. Each of these preparations was administered to rats and concentrations in blood were measured in the same manner as in Example 19 to obtain the results as shown in Table 14.

TABLE 14

| Preparation | Concentrations in blood (γ/ml) | | | |
|---|---|---|---|---|
| | 15 min. | 30 min. | 60 min. | 120 min. |
| Control (sodium chloride) | 0.9 | 1.8 | 0.3 | — |
| Present invention (D-phenylglycine/ sodium chloride) | 13.1 | 10.7 | 3.5 | 1.3 |
| Present invention (L-aspartic acid/ sodium chloride) | 8.4 | 10.3 | 2.8 | 0.9 |

EXAMPLE 21

Figure 8:
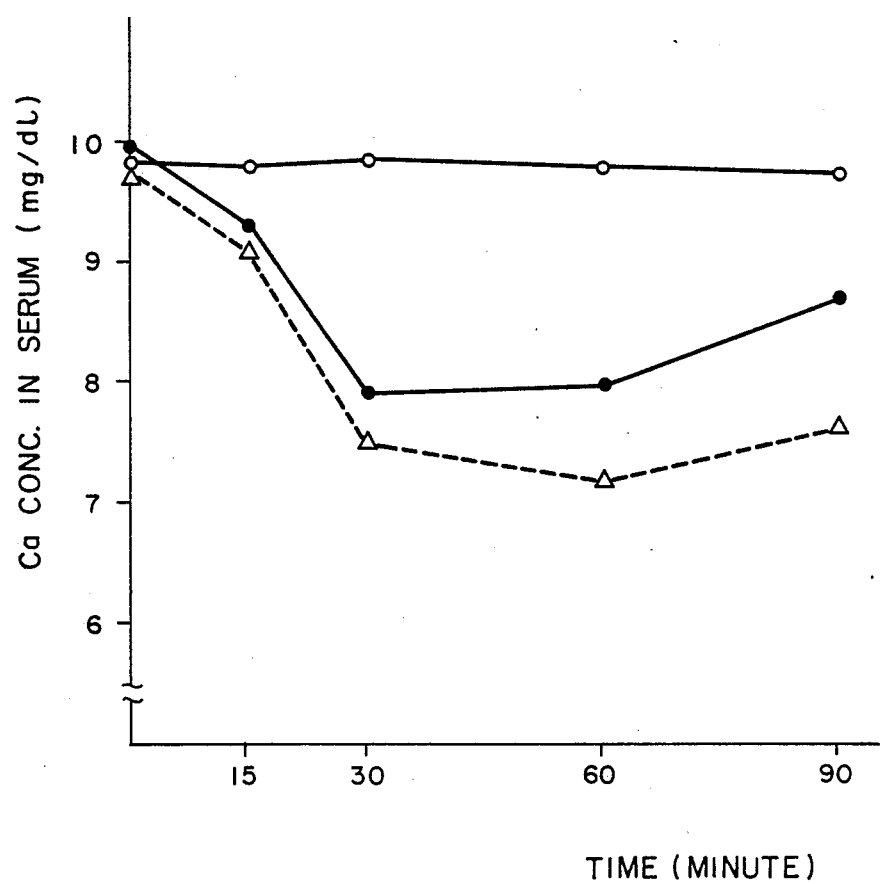
FIG. 8 is a curve of calcium concentration in serum when using Elcitonin as medicine.

Ten units of Elcitonin (Asu. (1.7) eel calcitonin) as medicine, pulverized EDTA.2Na (20 mg) as absorption promoter and pulverized sodium chloride as hypertonicator (50 mg) were dissolved in 5% gelatin solution to an amount of 1 g, which was then administered intrarectally to S.D. rats of four weeks of age each in an amount of 0.1 ml. Calcium concentrations in serum were measured 15 minutes, 30 minutes, 60 minutes and 90 minutes after administration according to the atomic absorption method. The same experiment was repeated except that 20 mg of CyDTA was employed in place of EDTA.2Na. Further, as Control, a preparation was prepared without use of the absorption promoter, followed by similar procedure. The results are shown in FIG. 8, in which ● — ● indicate calcium concentrations in serum in case of the preparation containing EDTA.2Na as absorption promoter of this invention, △—△ indicating calcium concentrations in serum in the case of the preparation containing CyDTA of this invention and further ○ — ○ indicating calcium concentration in serum in the case of the preparation as Control containing no absorption promoter.

EXAMPLE 22

Using ampicillin.Na (20 g potency) as medicine, sodium oxalate as absorption promoter (0.5 g) and sodium chloride (4 g) as water-soluble solution for hypertonic conditions, which are each pulverized, a homogeneous dispersion was prepared by adding these components to a base of 50 g of peanut oil, followed further by dilution with peanut oil to a total amount of 100 g. The preparation was then filled in aliquots each of 1 g in gelatin soft capsules.

EXAMPLE 23

Tuberactinomycin N sulfate (20 g), sodium chloride (3 g) as water-soluble substance for hypertonic conditions and sodium oxalate as absorption promoter (0.2 g), which were each pulverized, were added to an oily base of peanut oil to a total amount of 100 g to obtain rectal capsules.

EXAMPLE 24

Cefazolin.Na (200 g activity), D-phenylglycine (50 g) and sodium chloride (50 g) were each pulverized and mixed together. To the resulting mixture, there was added Witepsol W-35 melted by heating to 1 kg, followed by homogeneous dispersion. The dispersion was then molded in a suppository containing to provide suppositories each of 1 g.

EXAMPLE 25

Ampicillin.Na (250 g activity), D-phenylglycine (200 g) and sodium chloride (50 g), each being pulverized, were mixed and the resulting mixture was mixed with Witepsol H-15 melted by heating to an amount of 1 kg, which was further homogeneously dispersed. The dispersion was molded in suppository container to provide suppositories each of 1 g.

EXAMPLE 26

Finely pulverized ampicillin.3H$_2$O (250 g activity), α-ketobutyric acid (100 g) and finely pulverized sodium chloride (50 g) were mixed together. The resulting mixture was mixed with Witepsol W-35 melted by heating to an amount of 1 kg, followed by homogeneous dispersion. Suppositories each of 1 g were molded in suppository containers.

EXAMPLE 27

Finely pulverized Cephalothin.Na (250 g potency), ethyl aceto acetate (100 g) and finely divided sodium chloride (50 g) were mixed with sesame oil to an amount of 1 kg to form a homogeneous dispersion. The dispersion was filled in aliquots each of 2 g into plastic injection cylinders to obtain intrarectal injection preparations.

EXAMPLE 28

Tuberactinomycin N sulfate (500 g potency), oxaloacetic acid (100 g) and sodium chloride (50 g) were each pulverized and mixed. The mixture was mixed and homogeneously dispersed with Witepsol H-5 melted by heating to an amount of 1 kg. The dispersion was molded in suppository containers to provide suppositories (each 2.5 g).

EXAMPLE 29

One hundred thousand units of Elcitonin, 20 g of finely pulverized CyDTA and 50 g of finely pulverized sodium chloride were added to Witepsol H-15 melted by heating to an amount of 1 kg, and the resulting mixture was molded in aliquots each of 1 g in suppository containers to provide suppositories (1 g).

EXAMPLE 30

One hundred thousand units of Elcitonin, 30 g of finely pulverized sodium phenylpyruvate and 250 g of finely pulverized mannitol were dispersed by dissolution in 0.1% carboxyvinyl polymer solution (Wako Gel, trade name, produced by Wako Junyaku Co., Ltd.) to an amount of 1 kg, which was then injected into plastic applicators in aliquots each of 1 g to provide intrarectal injection preparations.

EXAMPLE 31

Gentamycin (200 g activity), sodium caproate (50 g) and sodium chloride (50 g) were each finely divided and mixed together. The mixture was mixed with Witepsol W-35 melted by heating to an amount of 1 kg, and the resulting mixture was molded in suppository containers to provide 1 g suppositories.

EXAMPLE 32

Amicacin sulfate (200 g activity), α-ketoglutamic acid (50 g) and sodium chloride (50 g) were each finely divided and mixed together, and Witepsol H-15 melted by mixing was added to the mixture to an amount of 1 kg. Further, the resulting mixture was molded in suppository containers to provide 1 g suppositories.

EXAMPLE 33

To 50 mg of finely pulverized HAPA-B.H$_2$SO$_4$, added was heat-melted Witepsol H-15 (dynamite Nobel Co.) to make a total amount of 1 g. The mixture was well stirred to form a homogeneous dispersion. The dispersion was filled in a silicone tube (inner diameter 2.5 mm) to produce a rod-like suppository of 50 mg (control). Separately, to the same preparation as above, added were 3.6% NaCl and 5% malic acid to obtain a suppository havign four fold tonicity (X4).

The suppositories were intraectally administered to S.D. male rats (weighing about 250 g) and the concentration of HAPA-B in blood was measured and the bioavailability was calculated. The results are shown in the following table.

The concentration of HAPA-B in blood was determined on sampled plasma by the use of *Bacillus subtilis* ATCC 6633 in accordance with the conventional method. (A relative activity of bioavailability is shown by a value where intramuscular injections of 50 mg of HAPA-B is assumed to provide 1.0)

The same experiments were effected on Tobramycin sulfate and Netromycin sulfate. The results are also shown in the following table 15.

TABLE 15

|  | Relative activity |
| --- | --- |
| HAPA-B 50 mg (control) | 1.0 |
| Four fold tonicity (X4) | 30.1 |
| Tobramycin sulfate 50 mg (control) | 2.1 |
| Four fold tonicity (X4) | 27.6 |
| Netromycin sulfate 50 mg (control) | 1.4 |
| Four fold tonicity (X4) | 25.7 |

EXAMPLE 34

To 75 g of finely pulverized carbenicilline.Na, added was heat-melted Witepsol H-15 to make a total amount of 1 g. The mixture was well stirred to form a homogeneous dispersion. The dispersion was filled in a silicone tube (inner diameter 2.5 mm) to produce a rod-like suppository of 50 mg as a control suppository. Separately, to the same preparation as above were added 3.6% NaCl and 5% sodium adipate to obtain a suppository of four fold tonicity (x4).

These suppositories were intrarectally administered to S.D. male rats (weighing about 250 g) and the concentration of Carbenicillin in blood was measured. The results are shown in the following table.

The concentration of Carbenicillin in blood was determined on sampled plasma by the use of *Sarcina luteus*

ATCC 9341 in accordance with the conventional method.

The same experiment was effected on Dicloxacillin.Na. The results are also shown in the following table 16.

TABLE 16

|  | Concentration in plasma (μg/ml) | | | | | | |
|---|---|---|---|---|---|---|---|
|  | 5 | 10 | 20 | 30 | 60 | 90 | 120 min. |
| Carbenicillin · Na 75 mg (control) | — | — | — | — | — | — | — |
| Four fold tonicity | 5.0 | 14.7 | 11.5 | 8.9 | 5.1 | 3.1 | 1.6 |
| Dicloxacillin · Na 75 mg (control) | — | — | — | — | — | — | — |
| Four fold tonicity | 4.5 | 15.4 | 10.5 | 7.5 | 4.6 | 2.9 | 0.9 |

(—: n.d.)

EXAMPLE 35

To 40 mg of finely pulverized Colistin methane sulfonate sodium, added was heat-melted Witepsol H-15 to make a total amount of 1 g. The mixture was well stirred to form a homogeneous dispersion. The dispersion was filled in a suppository container and molded to obtain a rectal suppository of 1 g (control). Separately, to the same preparation as above were added 3.6% NaCl and 5% sodium caprylate to obtain a suppository of four fold tonicity (X4).

These suppositories were intrarectally administered to white male rabbits (weighing 2.5–3 Kg) in an amount of 250 mg/Kg and the excreted amount of Colistin in urine was measured.

The measurement of amount of Colistin in urine was made using *Escherichia coli*. The same experiment was carried out on Polymyxin B. The results are also shown in the following table 17.

TABLE 17

|  | Excreted amount in urine (0–6 hr, %) |
|---|---|
| Colistin methanesulfonate sodium 40 mg (control) | 1.0 |
| Four fold tonicity (X4) | 49.1 |
| Polymyxin B 1 mg (control) | 0.8 |
| Four fold tonicity | 42.3 |

EXAMPLE 36

To 2000 U.S.P. of Heparin.Na, added was heat-melted Witepsol H-15 to make a total amount of 1 g. The mixture was well stirred to form a homogeneous dispersion. The dispersion was filled in a suppository container and molded therein to obtain a rectal suppository of 1 g (control). Separately, to the same preparation as above were added 2.7% NaCl and 5% oxaloacetic acid to obtain a suppository of three fold tonicity (X3) - -. While symbol -●- is control test results.

Figure 9:
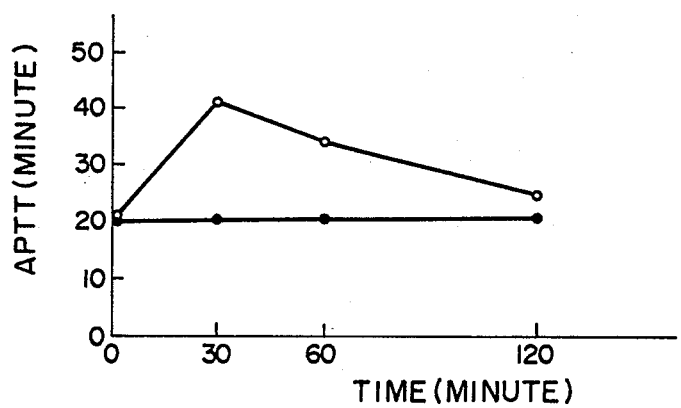
FIG. 9 shows APTT curves (Activated Partial Thromboplastin Time) of heparin.Na versus measurement time when heparin.Na is intrarectally administered to white male rabbits (weighting 2.5-3 kg) in an amount of 250 mg/kg.

These suppositories were intrarectally administered to white male rabbits (weighing 2.5–3 kg) in an amount of 250 mg/kg and activated partial thromboplastin time (APTT) was measured. The results are shown in FIG. 9.

EXAMPLE 37

To 0.12 g of finely pulverized lysozyme chloride, added was heat-melted Witepsol H-15 to make a total weight of 1 g. The mixture was well stirred to form a homogeneous dispersion. The dispersion was filled in a suppository container and molded therein to obtain a rectal suppository of 1 g (control). Separately, to the same preparation as above were added 2.7% NaCl and 5% phenylmalonic acid to obtain a suppository of three fold tonicity (X3).

These suppositories were intrarectally administered to white male rabbits (weighing 2.5–3 kg) in an amount of 250 mg/kg and the concentration of lysozyme in plasma was measured. The results are shown in the following table 18. The concentration of lysozyme in plasma was determined by bacteriolysis method.

TABLE 18

|  | Concentration in plasma (μg/ml) | | | | | |
|---|---|---|---|---|---|---|
|  | 15 | 30 | 45 | 60 | 120 | 180 min. |
| Control | — | — | — | — | — | — |
| X3 | 8.2 | 12.4 | 10.9 | 8.3 | 7.1 | 4.3 |

(—: n.d.)

EXAMPLE 38

50 mg of Orgotein was dissolved in 1 ml of an isotonic phosphate buffer of pH 7.5 (control solution). To this solution were added 5% α-keto-butyric acid and 27 mg of NaCl (X4) to prepare solutions. 0.2 ml of each solution was intrarectally administered to S. D. male rats (weighing about 250 g) and the concentration of Orgotein in blood was measured and the area under the curve of concentration in serum with time until 2 hrs is shown in the following table 19. The concentration of Orgotein in serum was determined on the sampled serum by the enzyme immunoassay in accordance with the conventional method.

TABLE 19

|  | $AUC_0^2$ (hr · g/ml) |
|---|---|
| Control | n.d. |
| X4 | 5.7 |

Note:
$AUC_0^2$ = area under a blood level versus time curve from 0 to 2 hrs.

EXAMPLE 39

Figure 10:
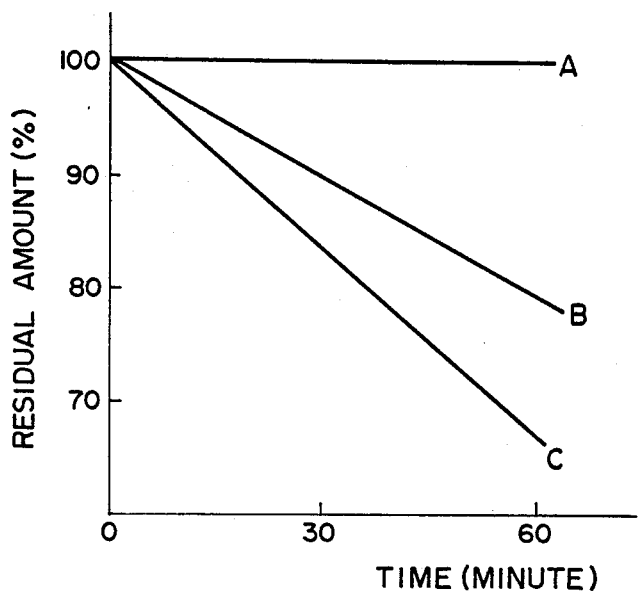
FIG. 10 shows curves plotting residual amount (%) of PTH versus measurement time.

Using 0.01% solution of PTH (in 0.1M tris-HCl buffer, pH 7.5), rectal circulation experiment was conducted on S.D. male rats (weighing 200–250 g) according to the Kakemi et al method (chem. Pharm. Bull. 13(7)861, 1965) and residual amount of PTH was measured with time. The results are shown in FIG. 10.
Sample A (control):
  0.01% PTH
  0.9% NaCl
Sample B:
  0.01% PTH
  0.5% N-Phenylglycine Na
  1.8% NaCl
Sample C:
  0.01% PTH
  0.5% N-Phenylglycine Na
  3.6% NaCl

EXAMPLE 40

To 0.1 g of finely pulverized 5-fluorouracil (5-Fu), added was heat-melted Witepsol H-15 to make a total amount of 1 g. The mixture was well stirred to form a homogeneous dispersion. The dispersion was filled in a silicone tube (inner diameter 2.5 mm) to produce a rod-like suppository of 50 mg (control). Separately, to the same preparation as above were added 3.6% NaCl and 5% ethyl acetoacetate to obtain a suppository of four fold tonicity (X4).

These suppositories were intrarectally administered to S.D. male rats (weighing about 250 g) and the concentration of 5-Fu in blood was measured. The results are shown in the following table 20.

The concentration of 5-Fu in blood was determined on sampled plasma using *Staphylococcus aureus* in accordance with the conventional method.

TABLE 20

| | Concentration in blood (μg/ml) | | | | | |
|---|---|---|---|---|---|---|
| | 5 | 10 | 20 | 30 | 60 | 120 min. |
| Control | — | — | — | — | — | — |
| X4 | 6.3 | 9.5 | 5.1 | 1.7 | 0.9 | 0.3 |

(—: n.d.)

EXAMPLE 41

Figure 11:
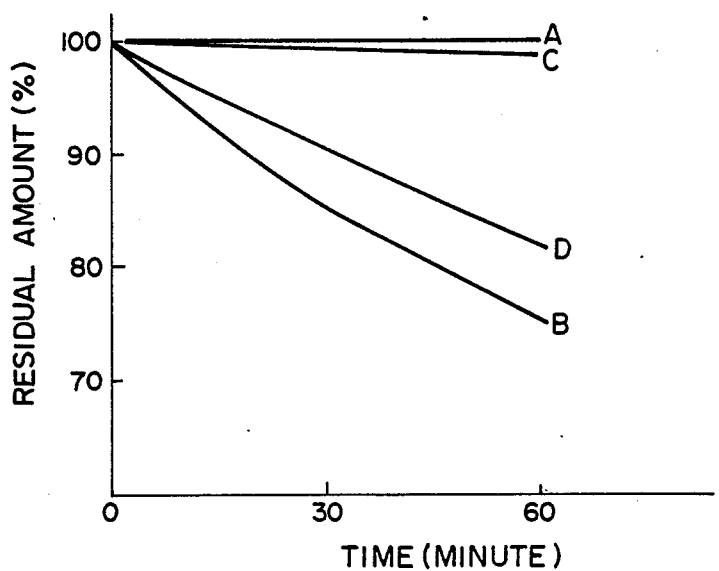
FIG. 11 shows curves plotting residual amount (%) of neplanocin-A and neplanocin-C versus measurement time.

Using 0.1% solution of Neplanocin-A and Neplanocin-C (in 0.1M Tris-HCl buffer, pH 7.5), rectal circulation experiment were conducted on rats (weighing 200-250 g) in accordance with the Kakemi et al method and residual percentages of Neplanocin-A and Neplanocin-C were measured with time. The results are shown in FIG. 11. Measurements were carried out by HPLC.

Sample A (control):
0.1% Neplanocin A
0.9% NaCl

Sample B:
0.1% Neplanocin A
0.5% α-ketoglutaric Na
3.6% NaCl

Sample C (control):
0.1% Neplanocin C
0.9% NaCl

Sample D:
0.1% Neplanocin C
0.5% ketomalonic Na
3.6% NaCl

EXAMPLE 42

Figure 12:
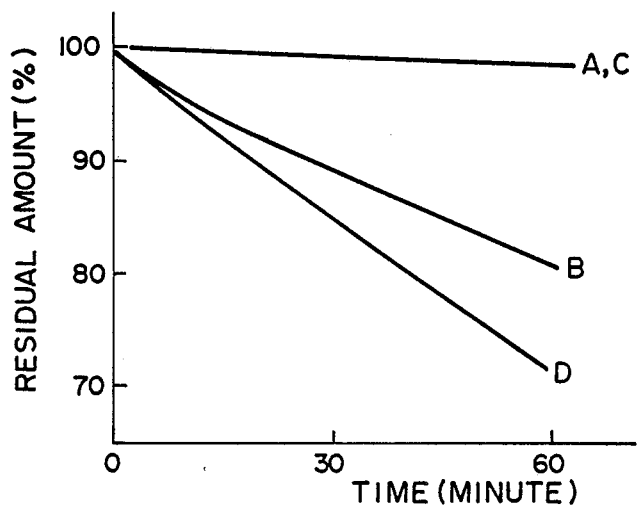
FIG. 12 shows curves plotting residual amount (%) of Ara-C and Ara-A versus measurement time.

Using 0.1% solutions of Ara-C and Ara-A (in 0.1M Tri-HCl buffer, pH 7.5), rectal circulation experiments were conducted on rats (weighing 200-250 g) in accordance with the Kakemi et al method and residual percentages of Ara-C and Ara-A were measured. The results are shown in FIG. 12. Measurements were carried out by HPLC.

Sample A (control):
0.1% Ara-C
0.9% NaCl

Sample B:
0.1% Ara-A
0.1% DL-glutamic acid
3.6% NaCl

Sample C (control):
0.1% Ara-C
0.9% NaCl

Sample D:
0.1% Ara-A
0.1% DL-phenylglycine
3.6% NaCl

What is claimed is:

1. A rectal composition for promoting improved absorption of medicine through the rectum containing a therapeutically effective amount of water soluble peptide hormone, and additionally containing:

(a) from 0.1 to 50 w/w % of at least one water soluble chelating agent selected from the group consisting of oxalic acid, malonic acid, glutaric acid, maleic acid, adipic acid, fumaric acid, trans-asonitic acid, pimelic acid, ethylmalonic acid, iminodiacetic acid, nitrilotriacetic acid, malic acid, lactic acid, glycero-3-phosphoric acid, fructose-1,6-diphosphoric acid, glucuronic acid, galacturonic acid, glyoxylic acid, oxaloacetic acid, α-ketobutyric acid, pyruvic acid, α-ketoglutaric acid, levulinic acid, 3-phenylacetylacetone and ethylacetoacetate, and their salts and their esters, and (b) at least 1 w/w % of a water soluble solute selected from the group consisting of halides, sulfates, phosphates, nitrates amd carbonates of alkali metals, the total concentration of the dissolved chelating agent and solute in an aqueous medium being sufficient so that the composition exhibits an osmotic pressure of 1.5 to 7 times greater than that of isotonic sodium chloride solution.

2. A rectal composition according to claim 1, wherein said water soluble peptide hormone is calcitonin.

3. A rectal composition according to claim 1, wherein said composition is in the form of a suppository which further comprises an oily vehicle or a water soluble vehicle.

4. A rectal composition according to claim 1, wherein said water soluble solute is selected from the group consisting of sulfates, phosphates, nitrates and carbonates of alkali metals.

5. A rectal composition according for promoting improved absorption of medicine through the rectum containing a therapeutically effective amount of water soluble peptide hormone, and additionally containing:

(a) from 0.1 to 50 w/w % of at least one water soluble chelating agent selected from the group consisting of oxalic acid, malonic acid, glutaric acid, maleic acid, adipic acid, fumaric acid, trans-aconitic acid, pimelic acid, ethylmalonic acid, iminodiacetic acid, nitrilotriacetic acid, malic acid, lactic acid, glycero-3-phosphoric acid, fructose-1,6-diphosphoric acid, glucuronic acid, galaturonic acid, glyoxylic acid, oxaloacetic acid, α-ketobutyric acid, pyruvic acid, α-ketoglutaric acid, levulinic acid, 3-phenylacetylacetone, and ethylacetoacetate, and their salts and their esters, and (b) at least 0.25M of a water soluble solute selected from the group consisting of mono- and di-saccharides, the total concentration of dissolved chelating agents and solute in an aqueous medium being sufficient so that the composition exhibits an osmotic pressure of 1.5 to 7 times greater than that of isotonic sodium chloride solution.

6. A rectal composition according to claim 5, wherein said water soluble peptide hormone is calcitonin.

7. A rectal composition according to claim 5, wherein said composition is in the form of a suppository which further comprises an oily vehicle or a water soluble vehicle.

8. A preparation according to claim 5 wherein the water-soluble saccharide is sorbitol, glucose, mannitol, maltose, lactose or sucrose.

9. A preparation according to claim 1 wherein the water-soluble peptide hormone has a partition coefficient of 50 or less in chloroform/water.

10. A preparation according to claim 1 wherein the amount of water soluble chelating agent is in the range from 1.0 to 30 W/W %.

11. A preparation according to claim 1 wherein the amount of water soluble is in the range of from about 2 to 30 W/W %.

12. A preparation according to claim 5, wherein the water-soluble peptide hormone has a partition coefficient of 50 or less in chloroform/water.

13. A preparation according to claim 5 wherein the amount of water soluble chelating agent is in the range from 1.0 to 30 W/W %.

* * * * *